(12) United States Patent
Horian

(10) Patent No.: US 6,769,436 B2
(45) Date of Patent: Aug. 3, 2004

(54) VOLATILE INHALER AND METHOD

(76) Inventor: Richard C. Horian, 11952 Montana Ave., #102, Los Angeles, CA (US) 90049-5030

(*) Notice: Subject to any disclaimer, the term of this patent is extended or adjusted under 35 U.S.C. 154(b) by 0 days.

(21) Appl. No.: 10/187,260

(22) Filed: Jun. 28, 2002

(65) Prior Publication Data

US 2004/0055613 A1 Mar. 25, 2004

(51) Int. Cl.[7] .............................................. A24F 47/00
(52) U.S. Cl. .................. 131/273; 131/270; 128/202.21
(58) Field of Search ................................ 131/270, 273; 128/202.21, 200.24, 203.12; 604/518.85; 239/33; 426/85

(56) References Cited

U.S. PATENT DOCUMENTS

| | | | | |
|---|---|---|---|---|
| 2,445,476 A | * | 7/1948 | Folkman ..................... | 131/273 |
| 2,901,357 A | * | 8/1959 | Epstein ........................ | 426/85 |
| 3,254,471 A | * | 6/1966 | Morham ..................... | 53/374.8 |
| 3,757,798 A | * | 9/1973 | Lambert ..................... | 131/270 |
| 3,990,872 A | * | 11/1976 | Cullen ............................. | 96/6 |
| 4,537,308 A | * | 8/1985 | Hollander, Jr. .............. | 206/484 |
| 4,860,929 A | * | 8/1989 | Lowe et al. ................... | 99/323 |
| 4,928,632 A | * | 5/1990 | Gordon ....................... | 119/709 |
| 5,167,242 A | * | 12/1992 | Turner et al. ............... | 131/273 |
| 5,431,915 A | * | 7/1995 | Harvey et al. .............. | 424/439 |
| 5,718,681 A | * | 2/1998 | Manning ..................... | 604/518 |
| 6,176,371 B1 | * | 1/2001 | Tyrrell ........................ | 206/204 |
| 6,258,384 B1 | * | 7/2001 | Stanley et al. .............. | 424/600 |

* cited by examiner

Primary Examiner—Dionne A. Walls
(74) Attorney, Agent, or Firm—Fulbright & Jaworski L.P.

(57) ABSTRACT

An inhaler for dispensing volatile ingredients including a one piece tube pinch closed and sealed at the ends. The tube may include reservoirs formed therein and noncircular cross sections. A volatile or volatiles such as nicotine and/or flavoring and/or medication are loaded in the tube with or without other ingredients and the ends closed. Absorbent material may be used to retain more volatiles within the tube or better wick the volatile vapors when air is drawn through the tube. A cutter including a body, a blade slidable in a longitudinal path within the body and a slot access receiving the pinch closed and sealed ends of the tube allow the ends of the tube to be cut off. Drawing air through the tube transfers vapors of the volatile or volatile including other ingredients from the interior of the tube to the user.

12 Claims, 4 Drawing Sheets

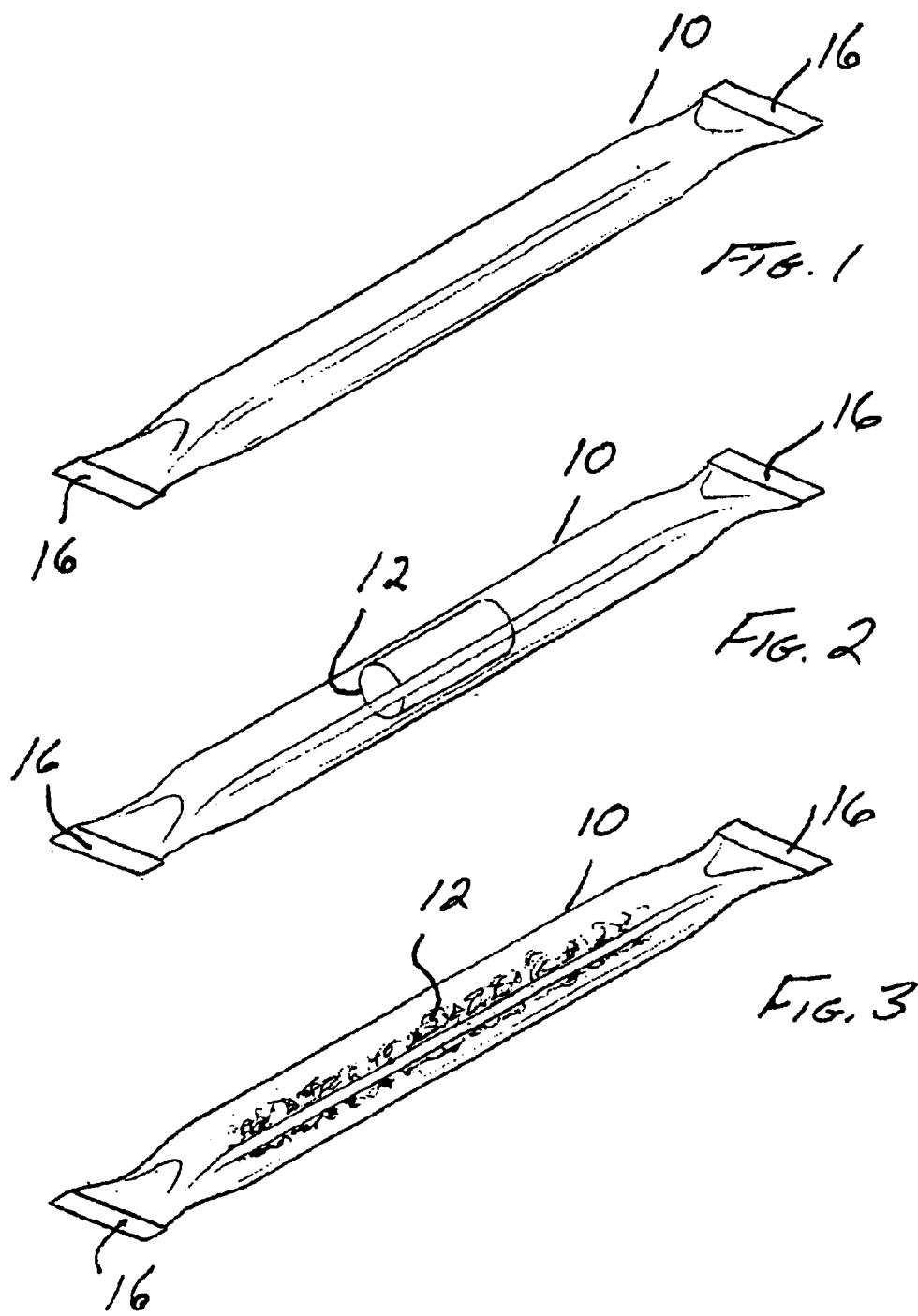

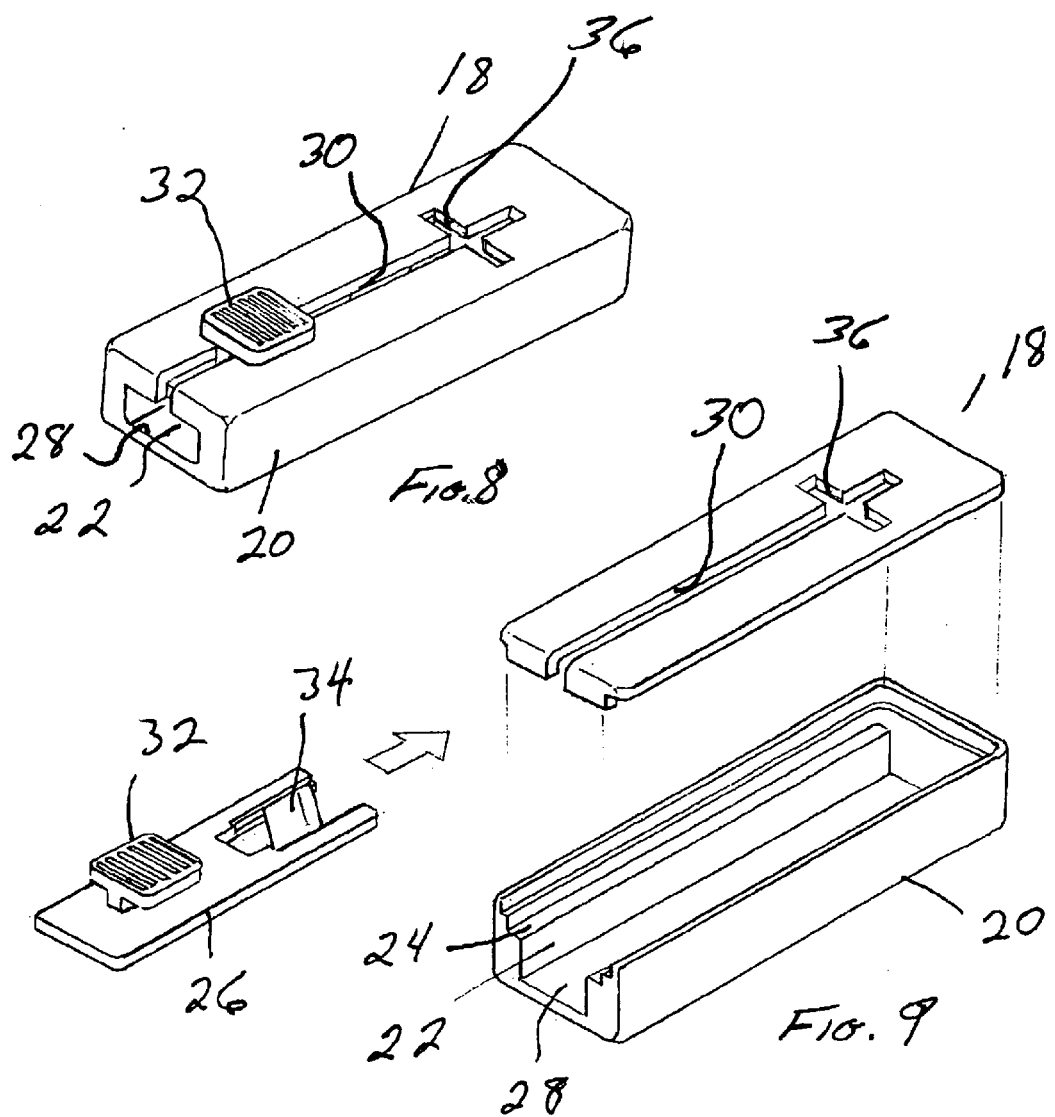

VOLATILE INHALER AND METHOD

BACKGROUND OF THE INVENTION

The field of the present invention is inhaler delivery systems for volatiles.

Tobacco smoking is blamed for hundreds of thousands of deaths each year. Further, second hand smoke inhaled by others is also blamed for serious health problems. Tobacco smoke also contains many known carcinogens, gasses and particulates that are harmful to ones health. There have been many products attempting to help people quit smoking. However, millions are unable to break the habit. One of the main reasons for this is that tobacco smoke contains nicotine which is believed to be highly addictive.

An object of many smoking cessation aids and nicotine therapy products is to deliver to the user a dose of nicotine without the many deleterious effects of smoke found in burning tobacco. Nicotine inhalers are growing in popularity as a device to deliver nicotine vapor or gasses through inhalation to the user without damaging smoke.

One advantage to inhalers is that it more closely resembles the act of smoking. Such inhalers deliver a dose of nicotine directly to the mucous membrane of the mouth and or lungs where it is absorbed quickly and transferred to the brain to satisfy the craving for nicotine. Another advantage to nicotine inhalers is that they can be made in a similar shape and size to that of a cigarette to more closely resemble the act of smoking a lit cigarette. Additionally, inhalers can provide the "hit" upon demand of a sudden dose of delivered nicotine to the user that is similar to a lit cigarette.

An estimate recently made by a major cigarette filter manufacturer concluded that the global consumption of cigarettes in 1999 was 5.7 trillion. A modern cigarette manufacturing line produces 14,000 cigarettes each minute. Not only do ignitable cigarettes efficiently deliver nicotine, they can be manufactured at a rate and cost sufficient to satisfy the demand. Available nicotine inhalers have not matched the efficiency and low cost production of modern cigarette manufacturing.

Of the many different nicotine inhaler designs known, all have something in common. The outer container that houses the nicotine delivery system or nicotine content is sealed from the atmosphere by an independent means, action or system that is additional to the primary nicotine container itself. Whether it is an additional package wrapping, internal valve sealer, removable cap or heat sealed nicotine impermeable tabs that are designed to be punctured or removed; all have an additional step or series of components designed to keep the primary nicotine impermeable container sealed from the atmosphere. The reason for this is that nicotine is a volatile substance and will degrade rapidly when exposed to the atmosphere unless the container of the inhaler is properly sealed.

SUMMARY OF THE INVENTION

The present invention is directed to an inhaler of volatiles. The inhaler includes a one piece tube containing a volatile substance. The tube is pinch closed at the ends to form a sealed chamber. Access to the volatiles is accomplished by removing the pinched ends so that the user may draw through the tube to inhale the volatile. The volatile may include, inter alia, nicotine and/or a flavoring or medicant. Depending on need, an absorbent element may provide a storage matrix for the volatile.

The tube typically has a cylindrical cross section but may deviate therefrom to increase the ratio of tube surface area to cross-sectional area for increased delivery. Reservoirs may be incorporated into the body of the tubing for added storage of volatiles. The ends are most conveniently sealed by heat and may be torn with scoring or cut to access the volatile.

The invention may also contemplate a cutter. The cutter includes a body having a longitudinal path. A blade is mounted to slide along the path within the body. There is a slot access in the body to the path which is sized to closely receive one of the pinch closed and sealed ends. The body may have a passage open at one end and extending to the slot.

The invention includes a method for dispensing volatile nicotine by cutting the ends of a sealed one piece tube and drawing air through the tube.

Accordingly, it is an object of the present invention to provide an improved volatile inhaler. Further objects and advantages will appear hereinafter.

BRIEF DESCRIPTION OF THE DRAWINGS

FIG. 1 is a perspective view of a volatile inhaler.

FIG. 2 is a perspective view of a volatile inhaler.

FIG. 3 is a perspective view of a volatile inhaler.

FIG. 8 is a perspective view of a second cutter.

FIG. 9 is an exploded assembly perspective view of the second cutter.

DETAILED DESCRIPTION OF THE PREFERRED EMBODIMENTS

Figure 4:
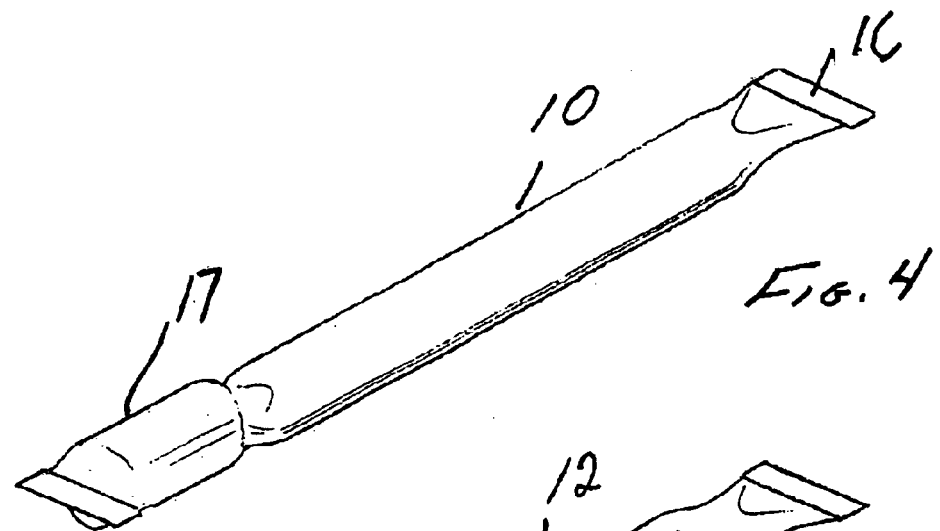
FIG. 4 is a perspective view of a volatile inhaler.

A volatile delivery inhaler is disclosed providing manufacture at the lowest cost and with the greatest degree of efficiency. The preferred embodiment may be employed with any volatile or volatiles but nicotine is first contemplated. Science and invention has helped millions of people to quit smoking. Yet many more millions are unable to quit and thousands of new people join the ranks of smokers each day. Cost is one of the key areas of smoking cessation or replacement products that has been overlooked. A low cost, yet effective, nicotine inhaler could add incentive to many people to replace their ignitable cigarettes with an alternative product that does not produce health damaging smoke with its many harmful elements. The method of use of the package can more closely mirror the ritual of smoking to help people more easily make the transition away from cigarettes.

The volatile inhaler of FIG. 1 is a one piece tube 10 of relatively uniform wall thickness. The tube 10 may be extruded, molded or fabricated out of flat stock and then rolled and sealed into a formed tube. The tube 10 may be of a single material, such as the barrier plastic manufactured by B.P.-Sohio under the trade name Barex, or it may be a multi-layer composition with similar barrier properties. Barex is an engineered barrier plastic designed by B.P.-Sohio used by many food and drug manufacturers to preserve volatile and or perishable chemicals and foods in the packaging process. It has been used for many different package seal applications. There are many other barrier plastics currently available and many more in development. The tube is impermeable to nicotine but is not limited to Barex. Any thermoplastic, metal, composite or combination of materials that are impervious to nicotine and other chemical, gas, flavoring or ingredient desired to be included within the tube may be used.

An extruded tube 10 made of Barex is disclosed in FIG. 1 with a wall thickness of 0.002" through 0.020". The tube 10 may be formed in a circular (FIGS. 1–3) or noncircular (FIGS. 4–6) cross section. A noncircular cross section increases the ratio of circumference to cross-sectional area. This increases interior tube surface area to the amount of air drawn over that surface area for increased density of volatiles in the air stream. The extrusion is then cut into lengths between 1" through 5" to most closely resemble the length of commercially available cigarettes.

Once cut, the tube 10 is then loaded with ingredients comprising the volatile delivery system. Folkman U.S. Pat. No. 2,445,476 issued Dec. 29, 1944 was one of the first to teach loading a plastic tube with absorbent materials saturated with ingredients meant for inhalation to simulate smoking without flammable ignition. This was followed by Bartolomeo U.S. Pat. No. 2,860,630 issued Nov. 18, 1958 who taught the concept of a saturated plug being inserted into a tube to offer both non-ignitable gaseous delivery of ingredients as well as an air restriction to simulate the restricted draw of a cigarette.

Figure 5:
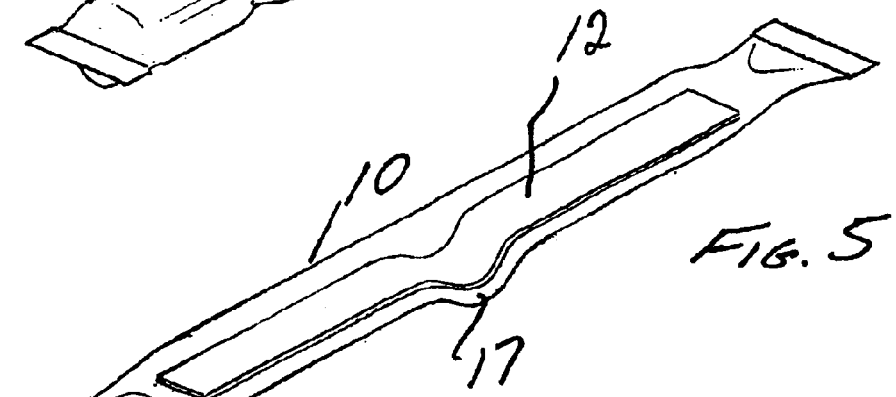
FIG. 5 is a perspective view of a volatile inhaler.

Any absorbent material 12 (FIGS. 2, 3, 5) compatible with the volatile or volatiles employed may be inserted into the tube 10 for best delivery to the user. The material 12 can be in the form of a plug (FIG. 2) of any density, small pieces (FIG. 3), or a strip (FIG. 5). Tobacco itself may be included in shreds or strip form within the tube 10 (FIG. 3) as an added flavorant or added source of nicotine providing the end product is not designed to be ignited. The tobacco may be moistened or saturated to provide the volatile required.

In one preferred embodiment, a tube 10 made of Barex was extruded with a 0.006" wall thickness. The tube was then cut to a 3.875" length. The tube was then loaded with 4 mg of USP grade liquid nicotine provided by Siegfried Ltd. of Switzerland. Liquid nicotine is a volatile substance with a vapor pressure of 0.53 mbr at 25 degrees C. The liquid nicotine may be loaded within the tube via spray or direct injection. The nicotine may be loaded into the tube in a gaseous atmosphere, such as nitrogen or other gas, conducive to preserving the nicotine. With spray or direct injection, the liquid nicotine migrates throughout the surface area of the inside of the tube regardless of the method of liquid nicotine insertion. The fluid mechanic principals of adhesion, cohesion, capillary action and surface tension cause a very evenly coated thin film of liquid nicotine to be coated over the entire surface area of the inside of the tube.

The one piece tube is then pinch closed at the two open ends 16 and heat sealed. Barex has excellent heat sealing properties and may be heat sealed by RF, impulse heat sealing, heated roller and direct platen methods of heat sealing. The heat seal affected at the two ends 16 is sufficient to exclude the open atmosphere from entering the tube 10 or the ingredients within the tube from escaping to the atmosphere.

Figure 6:
FIG. 6 is a perspective view of a volatile inhaler.

FIGS. 4 through 6 also show variations in the configuration of the tube 10. FIG. 4 illustrates a reservoir 17 which may simply include a volatile or may include absorbent material 12 holding the volatile and/or other ingredients. FIG. 5 illustrates another form of reservoir 17 and FIG. 6 illustrates a means for increasing the ratio of circumference to cross-sectional area by tacking the tube together diametrically.

Figure 7:
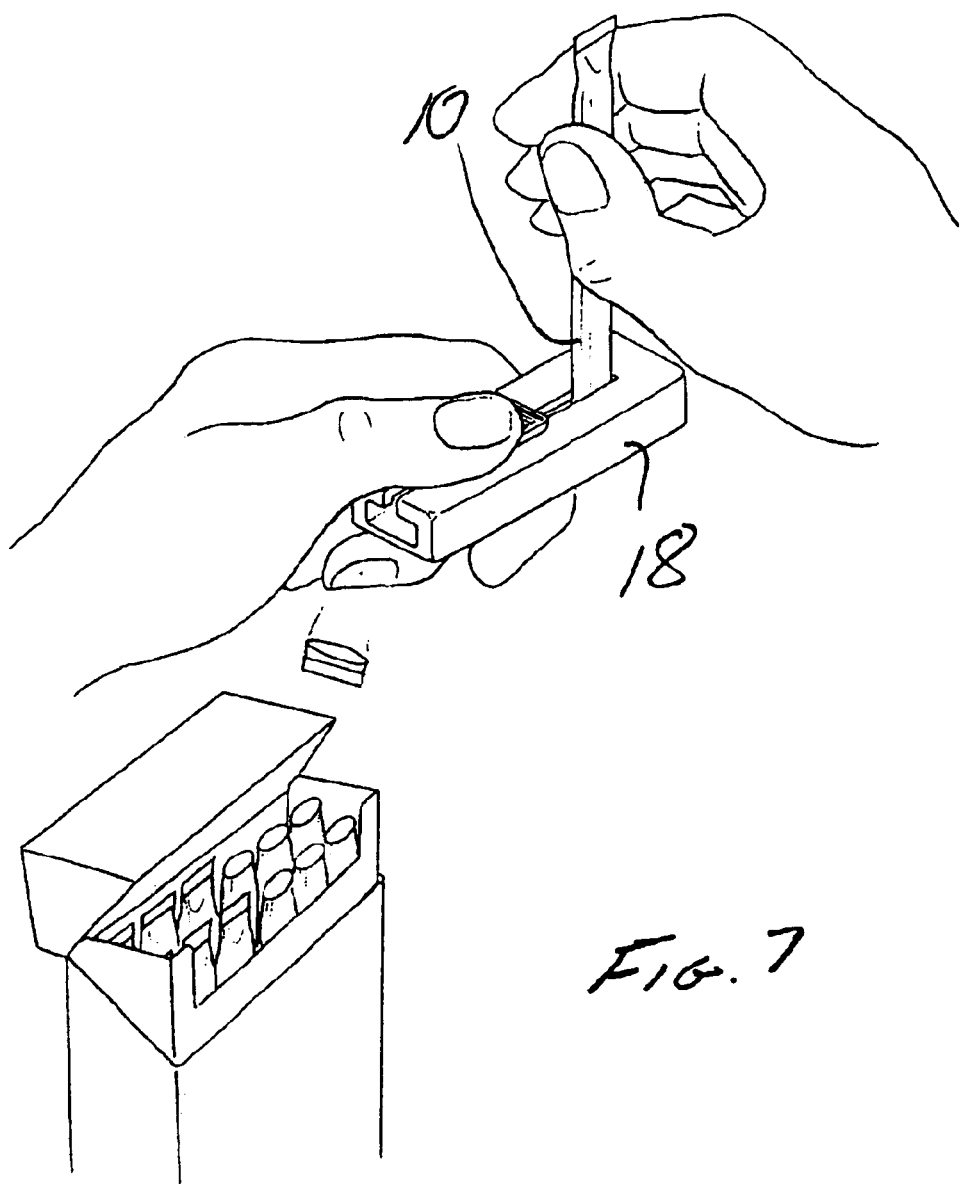
FIG. 7 is a perspective view of a pack of volatile inhalers, a first cutter and a volatile inhaler being cut by a user.

A separate cutter device 18 is provided to slice off the heat-sealed ends 16 of the tube 10 when ready for use. The cutter 18 may be esthetically very similar in shape to the commonly used cigarette lighter required to ignite a cigarette. The cutter 18 includes a body 20 having a longitudinal path 22. This configuration is most conveniently achieved by using a two piece body to define the path 22. The path 22 includes ways 24 to receive a blade holder 26. The ways 24 are set above the bottom of the path to define a passage 28 open at one end of the body 20. An access 30 runs along the path 22 through one wall of the body 20 in the cutter 18. The blade holder 26 slides on the ways 24 and has a thumb element 32 extending through the access 30 allowing forceful advance of the holder 26. A blade 34 is at a bias at the leading edge of the holder to cut anything extending into the path thereof. In the cutter 18 of FIG. 7, the access 30 terminates in a portion defining a slot receiving an end of the tube 16. In FIGS. 8 and 9, a slot 36 is arranged perpendicularly to the access 30 to extend across the path of the blade 34.

One end 16 of the tube 10 is inserted into the cutter slot 36 provided in the body 20 of the cutter 18 and thumb element 32 is advanced in the cutter to engage the blade 34 with the end 16. This cuts off the end 16 of the tube 10 inwardly of the seal area. Both ends 16 are cut off.

Use of the cutter 18 to prepare the tube 10 for inhalation is similar to the ritual of lighting a cigarette before inhalation and helps the smoker trying to quit by providing a similar hand ritual preparation of the tube 10 as in smoking.

When both ends 16 of the tube 10 are cut off, the tube 10 is then ready for inhalation of vapors produced by the volatiles. Adhesion evenly holds the microscopically thin film to the surface area of the inside of the tube regardless of the position the user holds the tube. The user then draws air through the tube 10 and the nicotine and/or other vapors included enter the mouth coming into contact with the mucous membrane lining of the inner mouth. Nicotine is transferred very quickly from the capillaries of the mucous membrane to the brain. The effect is very similar to the nicotine "hit" received when smoking a cigarette.

The extruded tube 10 with the extremely thin coating of nicotine or other volatile covering only the inside wall of the tube 10 offers excellent child protection. A child's fingers or tongue are not able to deeply enter the small diameter tube to extract any substantial level of nicotine. The cutter is also child resistant as the opening allowed to accept the heat sealed tube ends for cutting is only about 0.060"; far to small an opening to insert a finger or any other body part.

The manufacturing process allows a cost to effectively compete with cigarette manufacturing. The Barex tube at 0.300"×3.875"×0.006" wall thickness allows approximately 1000 tubes to be made per pound of plastic. At current market prices for Barex plastic, it equates to less then $0.002 per nicotine inhaler tube. A pack of 20 nicotine inhaler tubes, to equal a pack of cigarettes, can be made for a material cost of less than $0.30 including the added USP grade liquid nicotine at 0.5 mg through 25 mg per tube inhaler. Extrusion of the Barex plastic into the tube form can be accomplished at very high volume. The ingredients required to be included within the tube and the heat sealing process of the tube can all be accomplished in line at very high speeds.

It is important to note that a very rugged package is provided by this device. If the tube wall thickness is chosen to be 0.006", that means that the pinched wall heat sealed section will be a full 0.012" thick. The container ends at double the thickness of the tube wall are far less prone to being accidentally opened then previous inventions that include one half or far less in wall thickness of closure seal material. In fact, the sealed 0.006" tube requires scissors, a knife or the invented cutter as described to open the tube for use. The thin foil or thin film plastic closures described in previous inventions can be punctured by a child using the end of a paper clip.

There are other means available to accomplish the opening of the tube ends when ready for use besides the cutting of the ends. The heat sealed end closures could be perforated or scored near the heat seal to allow physical tearing of the seal. The heat sealed ends could also be punctured with a punch to open an airway.

Nicotine powder may also be used as one possible volatile. Adhesion allows the liquid nicotine to adhere to the inner walls of the tube without running out. Other ingredients may be included such as menthol, flavorings or other chemical enhancements. In fact, nicotine may be excluded altogether and a composition of volatile oils and or other ingredients and flavorings may be included to simulate the effect of nicotine and smoking without the addictive effects of a nicotine additive. Additionally, a medication may solely be included within the inhaler tube. The invention could thus be used as a fast and convenient method to inhale medication for conditions of asthma, bronchial congestion and other respiratory ailments.

The tube cutter is first used to sever the ends of the heat sealed inhaler tube. The cutter has an opening on one side to allow the clippings to be easily transferred to the open pack containing the inhaler tubes. The cutter may also be designed with a closed end and include an openable section of the body 20 or the end of the body that allows storage of many clippings until disposal of all clippings contained therein is desired. The user may also be instructed to return all used inhaler tubes to the package after use and dispose of properly. The entire contents of the package is made of one material and therefore recyclable; tubes and end clippings, to be made into new plastic products without waste. It is believed that this will help to mitigate the tremendous existing pollution problem of millions of lit cigarette butts being tossed out of car windows. These openly discarded cigarette butts end up in waterways through storm drain systems. It is also well known that tossed lit cigarette butts are the cause many forest fires. The invention noted by Turner U.S. Pat. No. 6,098,632 issued Aug. 8, 2000 teaches a Barex tube loaded with a saturated polyethylene plug and sealed at both ends with a thin foil composite. These are dissimilar materials that would be subject to labor to separate for reclamation.

The user then draws on the inhaler tube just like an ordinary lit cigarette. Air is transferred through the tube coming into contact with the volatile liquid nicotine vapors and other ingredients coating the tube walls. As the entire inner tube wall is coated with the thin film of the liquid nicotine, the greatest surface area to air contact is achieved. The moving air picks up the evaporate of the thin oily coating and is transferred to the oral cavity where it is quickly absorbed into the capillaries of the mucous membrane. The user will have several puffs as in an ordinary cigarette before the complete evaporate is dissipated.

As noted above, the tube 10 may also be extruded in noncircular shapes such as an ellipse or oval. The tube is extruded with a wall thickness of approximately 0.006". Barex plastic is a relatively rigid thermoplastic material. Even at a 0.006" wall thickness, the tube will easily hold it's shape. At this thickness however, the tube can also be easily compressed by the user. By holding the tube during a draw, the user may choose to collapse the tube with fingers or teeth to achieve different draw effects. Depending on how much the tube is manually pinched by the user and how deep or aggressive the air draw is, the user has control over the force of the air stream and how much nicotine vapor is dispersed with any draw to accommodate their needs. If no draws are taken on the once opened tube, the nicotine will evaporate or degrade within the tube walls over time.

After the tube contents are depleted, the user returns the empty tube to the open pack until another is required. As a smoking cessation aid, the user may be instructed to use an inhaler tube only when the panic need for nicotine becomes too great. This way, the user has a product that can be used only in emergencies while they are ridding themselves of the habit of smoking and the dependence upon cigarettes. The transition from being a smoker to being a nonsmoker can therefore be made with much less anxiety as the nicotine inhaler of this invention is so closely related in form, ritual and effect to the deadly cigarettes still being used by millions.

Accordingly, a system of dispensing volatiles as an inhaler is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. An inhaler of volatile nicotine vapor, comprising a one piece tube pinch closed and sealed at the ends thereof, the one piece tube being impermeable to nicotine;

a volatile nicotine contained within the tube; and an element in tube absorbent of the volatile nicotine.

2. The inhaler of claim 1, the nicotine being in a liquid state.

3. The inhaler of claim 1, the nicotine being in a solid state as a powder.

4. The inhaler of claim 1, further comprising a volatile flavoring.

5. The inhaler of claim 1, further comprising a volatile medication.

6. The inhaler of claim 1, the tube being heat sealed at the ends.

7. The inhaler of claim 1, the tube between the ends having a bore with a cross section having a higher numerical ratio of circumference to cross-sectional area than a circle.

8. The inhaler of claim 1, the tube including reservoirs formed therein.

9. The inhaler of claim 1, the tubes including scoring across the tube adjacent the ends.

10. A method for dispensing volatile nicotine vapor from a tube having pinch closed and sealed ends, comprising cutting both ends of the tube to provide communication with the atmosphere; and drawing air through the tube with both ends cut before substantial volatile nicotine has escaped.

11. The method of claim 10 further comprising loading the tube with volatile nicotine;

pinch closing and heat sealing the ends of the tube after loading with volatile nicotine, and cutting including cutting off the pinch closed and sealed ends.

12. The method of claim 10 further comprising loading the tube with volatile medication.

* * * * *

(12) INTER PARTES REEXAMINATION CERTIFICATE (0208th)
United States Patent
Horian

(10) Number: US 6,769,436 C1
(45) Certificate Issued: Nov. 16, 2010

(54) VOLATILE INHALER AND METHOD

(76) Inventor: Richard C. Horian, 11952 Montana Ave., #102, Los Angeles, CA (US) 90049-5030

Reexamination Request:
No. 95/000,134, Mar. 10, 2006

Reexamination Certificate for:
Patent No.: 6,769,436
Issued: Aug. 3, 2004
Appl. No.: 10/187,260
Filed: Jun. 28, 2002

(51) Int. Cl.
*A24F 47/00* (2006.01)
*A61M 15/00* (2006.01)
*A61M 15/06* (2006.01)

(52) U.S. Cl. .................. 131/273; 131/270; 128/202.21
(58) Field of Classification Search .................. None
See application file for complete search history.

(56) References Cited

U.S. PATENT DOCUMENTS

| | | | | |
|---|---|---|---|---|
| 2,860,638 | A | * 11/1958 | Bartolomeo | 128/202.21 |
| 4,083,372 | A | 4/1978 | Boden | 131/8 |
| 4,284,089 | A | 8/1981 | Ray | |
| 4,800,903 | A | 1/1989 | Ray et al. | |
| 4,805,767 | A | 2/1989 | Newman | 206/219 |
| 4,813,437 | A | 3/1989 | Ray | |
| 4,938,236 | A | * 7/1990 | Banerjee et al. | 131/194 |
| 4,972,855 | A | * 11/1990 | Kuriyama et al. | 131/355 |
| 5,293,883 | A | * 3/1994 | Edwards | 131/270 |
| 5,845,649 | A | * 12/1998 | Saito et al. | 131/352 |
| 5,875,786 | A | 3/1999 | Chase | 131/270 |
| 6,098,632 | A | 8/2000 | Turner et al. | 131/270 |
| 6,109,272 | A | * 8/2000 | Saito et al. | 131/297 |
| 6,178,969 | B1 | * 1/2001 | St. Charles | 131/273 |
| 6,651,848 | B1 | 11/2003 | Redmond | 222/107 |
| 6,797,105 | B1 | 9/2004 | Schumann et al. | 156/282 |
| 2003/0168375 | A1 | 9/2003 | Jarvis et al. | 206/532 |

FOREIGN PATENT DOCUMENTS

JP 2190178 * 7/1990
WO WO 00/10795 3/2000

* cited by examiner

*Primary Examiner*—Stephen J Stein

(57) ABSTRACT

An inhaler for dispensing volatile ingredients including a one piece tube pinch closed and sealed at the ends. The tube may include reservoirs formed therein and noncircular cross sections. A volatile or volatiles such as nicotine and/or flavoring and/or medication are loaded in the tube with or without other ingredients and the ends closed. Absorbent material may be used to retain more volatiles within the tube or better wick the volatile vapors when air is drawn through the tube. A cutter including a body, a blade slidable in a longitudinal path within the body and a slot access receiving the pinch closed and sealed ends of the tube allow the ends of the tube to be cut off. Drawing air through the tube transfers vapors of the volatile or volatile including other ingredients from the interior of the tube to the user.

At the time of issuance and publication of this certificate, the patent remains subject to pending reissue application number 11/441,461 filed May 26, 2006. The claim content of the patent may be subsequently revised in the reissue proceeding.

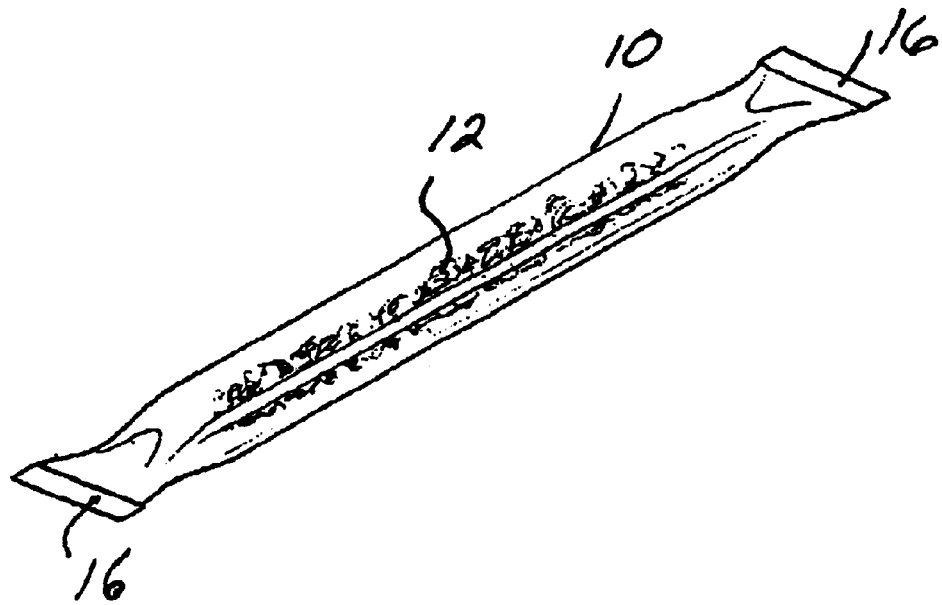

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2 and 3 are cancelled.

Claims 1 and 10 are determined to be patentable as amended.

Claims 4-9, 11 and 12, dependent on an amended claim, are determined to be patentable.

New claims 13-15 are added and determined to be patentable.

1. An inhaler of volatile nicotine vapor, comprising
 a one piece tube pinch closed and sealed at the ends thereof, the one piece tube being impermeable to nicotine;
 [a volatile nicotine contained within the tube; and
 an element in tube absorbent of the volatile nicotine]
 *a nicotine absorbent element in said tube that is absorbent of volatile liquid nicotine and consisting essentially of tobacco; and*
 *volatile liquid nicotine that has been added to said absorbent element contained within the sealed tube and in an amount sufficient to be absorbed by said element and moisten said tobacco.*

10. A method for dispensing volatile nicotine vapor from [a tube having pinch closed and sealed ends comprising] *an inhaler of volatile nicotine vapor, comprising: (a) a one piece tube pinch closed and sealed at the ends thereof, the one piece tube being impermeable to nicotine; (b) a nicotine absorbent element in said tube that is absorbent of volatile liquid nicotine and consisting essentially of tobacco; and (c) volatile liquid nicotine that has been added to said absorbent element contained within said tube and in an amount sufficient to be absorbed by said element and moisten said tobacco, said method consisting essentially of:*
 cutting both ends of the tube to provide communication with the atmosphere; and
 drawing air through the tube with both ends cut before substantial volatile nicotine has escaped.

*13. An inhaler according to claim 1, wherein said tobacco is saturated with liquid nicotine.*

*14. An inhaler according to claim 1, wherein said absorbent element consists essentially of shredded tobacco.*

*15. An inhaler according to claim 1, wherein said element comprises tobacco in strip form.*

* * * * *